United States Patent
Firlefijn et al.

(10) Patent No.: US 10,816,465 B2
(45) Date of Patent: Oct. 27, 2020

(54) OIL SENSOR FOR A COMPRESSOR

(71) Applicant: ATLAS COPCO AIRPOWER, NAAMLOZE VENNOOTSCHAP, Wilrijk (BE)

(72) Inventors: Jeroen Alois M. Firlefijn, Wilrijk (BE); Guido Jozef Christian Peeters, Wilrijk (BE)

(73) Assignee: ATLAS COPCO AIRPOWER, NAAMLOZE VENNOOTSCHAP, Wilrijk (BE)

( * ) Notice: Subject to any disclaimer, the term of this patent is extended or adjusted under 35 U.S.C. 154(b) by 411 days.

(21) Appl. No.: 15/567,485

(22) PCT Filed: Apr. 14, 2016

(86) PCT No.: PCT/BE2016/000019
§ 371 (c)(1),
(2) Date: Oct. 18, 2017

(87) PCT Pub. No.: WO2016/168901
PCT Pub. Date: Oct. 27, 2016

(65) Prior Publication Data
US 2018/0136124 A1    May 17, 2018

(30) Foreign Application Priority Data
Apr. 24, 2015  (BE) .................................. 2015/5273

(51) Int. Cl.
*G01N 21/552*  (2014.01)
*G01N 33/28*  (2006.01)
(Continued)

(52) U.S. Cl.
CPC ........... *G01N 21/552* (2013.01); *F01M 11/10* (2013.01); *F04B 39/02* (2013.01);
(Continued)

(58) Field of Classification Search
CPC .................................................. G01N 21/552
(Continued)

(56) References Cited

U.S. PATENT DOCUMENTS 4,553,032 A    11/1985   Lo et al.
4,988,195 A    1/1991    Walter
(Continued)

FOREIGN PATENT DOCUMENTS

DE    4038354 A1    6/1992
EP    2522984 A2    11/2012
GB    2105058 A     3/1983

OTHER PUBLICATIONS

International Search Report (ISR) dated Sep. 12, 2016, for PCT/BE2016/000019.

*Primary Examiner* — David P Porta
*Assistant Examiner* — Abra S Fein
(74) *Attorney, Agent, or Firm* — Bacon & Thomas, PLLC (57) ABSTRACT

An oil sensor comprising a holder to which an elongated crystal is fastened that is transparent to infrared light and with a refractive index greater than the refractive index of the oil to be examined, whereby a light source is provided in the holder at a first end of the elongated crystal for transmitting light in the infrared spectrum in the elongated crystal, and detector at a second end of the elongated crystal for measuring the intensity of the light, which during the passage through the elongated crystal undergoes total reflection at a boundary plane at least four times in succession in a contact zone where the elongated crystal comes into contact with the oil, wherein the oil sensor is further provided with at least one temperature sensor to determine the temperature of at least one of the components of the oil sensor.

20 Claims, 6 Drawing Sheets

(51) Int. Cl.
    *G01N 21/3577*    (2014.01)
    *G01N 21/85*    (2006.01)
    *F04B 39/02*    (2006.01)
    *F01M 11/10*    (2006.01)
    *G01N 21/27*    (2006.01)
    *G01N 21/05*    (2006.01)

(52) U.S. Cl.
    CPC ..... *F04B 39/0284* (2013.01); *G01N 21/3577* (2013.01); *G01N 21/8507* (2013.01); *G01N 33/2888* (2013.01); *F01M 2011/1466* (2013.01); *F04B 2201/0404* (2013.01); *F04C 2240/81* (2013.01); *F04C 2270/86* (2013.01); *F16N 2250/34* (2013.01); *G01N 21/05* (2013.01); *G01N 21/274* (2013.01); *G01N 2201/0221* (2013.01); *G01N 2201/06186* (2013.01)

(58) Field of Classification Search
    USPC .................................................... 250/339.01
    See application file for complete search history.

(56) References Cited

U.S. PATENT DOCUMENTS

| | | |
|---|---|---|
| 5,739,537 A | 4/1998 | Siesler et al. |
| 5,926,269 A | 7/1999 | Von Der Eltz et al. |
| 2001/0030288 A1 | 10/2001 | Wilks et al. |
| 2003/0175160 A1 | 9/2003 | Archibald et al. |
| 2004/0021849 A1 | 2/2004 | Kong et al. |
| 2004/0201835 A1 | 10/2004 | Coates et al. |
| 2010/0015714 A1 | 1/2010 | Saini et al. |

OIL SENSOR FOR A COMPRESSOR

The present invention relates to an oil sensor, in particular an oil sensor to determine the ageing of oil in a machine, more specifically in a compressor.

Compressor here means all types of gas and air compressors, such as centrifugal compressors, screw and tooth compressors, piston compressors, screw and roots blowers, vacuum pumps, as well as the respective expansion machines.

BACKGROUND OF THE INVENTION

Compressors are often provided with an oil circuit for the supply of oil to parts of the machine where lubrication and/or cooling is required. Mineral oil, semi-synthetic oil, synthetic oil, PAG oil or another oil can be used as an oil.

After fulfilling the lubrication and/or cooling function, the oil is collected in the oil circuit and made suitable again for lubrication and/or cooling purposes and then carried back to parts of the machine where lubrication and/or cooling is required.

In order to make the oil suitable again for lubrication and/or cooling purposes, the oil circuit is generally provided with a cooler in order to cool the oil and/or a filter system to remove contaminants from the oil.

Thanks to the presence of such a cooler and/or such a filter system in an oil circuit, a quantity of oil can be used for a long time in a compressor without new oil having to be put in the machine.

A problem that occurs is that the properties of the oil, i.e. the properties of the oil that are important for the lubricating and/or cooling action, such as for example the viscosity or other tribological properties, decrease due to degradation processes caused by repeated exposure of the oil to different conditions in the machine, i.e. degradation processes such as oxidation, temperature degradation and other ageing-causing processes.

In a compressor, oil is often not exclusively used to lubricate and cool mechanical components, such as bearings and gearwheels, but oil is also brought into the compression space in order to cool compressed gas, and to fulfil a sealing function between the rotor(s) and the housing of the compressor element. It is clear that whenever compressed gas is mentioned in this text, it can also mean a mixture of compressed gases such as compressed air for example.

After the compression, the oil is generally extracted from the compressed gas by means of an oil separator and then put back in the oil circuit.

In the compressor element the oil is mixed intensely with the gas, and the oil can also come into contact with any contaminants in the gas, which can accelerate the degradation processes.

If after the passage of time the properties of the oil are no longer adequate to ensure good lubrication and/or cooling action it can result in a degraded performance of the compressor, possibly wear and tear, and possibly even the failure of components of the compressor or the compressor as a whole.

For the aforementioned reasons the oil in a compressor must be replaced before the specified usage duration of this oil is reached and the properties of the oil could possibly be inadequate. A disadvantage is that during the replacement of the oil the compressor has to be taken out of service and that the replacement of the oil is expensive.

However, the conditions to which the oil can be exposed differ from machine to machine, for example by differences in operating regimes and/or different environmental factors. In a compressor a higher air humidity, for example, can lead to faster ageing of the oil.

The specified usage duration of the oil is determined such that, even with compressors in which the oil ages quickly, the oil will be replaced in good time. A disadvantage of this is that in compressors where the oil ages less quickly, the oil is replaced prematurely, or in other words before reaching the end of the lifetime, which leads to unnecessary costs.

In order to prevent this problem, the oil in the compressor can be checked to determine whether or not the oil is due for replacement.

This can be done for example by taking an oil sample, for example by using a test coupling, for example model SMK20 of Stauff. This enables an oil sample to be taken in a simple way, without the machine having to be taken out of service. Then the oil sample taken can be examined in a laboratory environment with special equipment in order to examine whether or not the oil needs replacing. For example, using infrared spectroscopy it can be determined whether certain constituents of the oil have decreased or even disappeared and whether other substances have got into the oil, due to degradation processes such as oxidation.

A disadvantage of such a method is that the taking of an oil sample, the transport of the oil sample to a laboratory, and then the performance of an analysis is very expensive and time consuming, and that all this has to be repeated at a later time when it has to be determined again whether the oil has since become due for replacement.

Various oil sensors are known for measuring the oil quality of engine oil in the oil circuit of a combustion engine, such as capacitive, inductive, magnetic, electrochemical or optical oil sensors. However, tests have shown that such oil sensors are insufficient to adequately determine the ageing of oil in a compressor.

The capacitive, inductive, magnetic and electrochemical oil sensors for engine oil can measure changes in the additives in the oil, but not, or insufficiently so, the small specific changes as a result of ageing in an oil with little or no additives, such as an oil for compressors.

While many additives are added to engine oil, generally few if any additives are added to the oil for compressors, because most additives do not remain active for the usage duration of oil for compressors that is typically substantially longer than that of engine oil. Indeed, oil in compressors can typically have a lifetime of several thousands of hours, while engine oil typically only lasts a few hundred hours.

Optical oil sensors for engine oil can measure specific changes, i.e. by measuring in a wavelength band in which molecules are excited which increase or decrease as a result of degradation processes so that the measurement is a measure of the ageing of the oil, but are not sensitive enough to measure small changes sufficiently accurately as a result of ageing of an oil for compressors over a long usage duration.

GB 2.105.058 describes an infrared spectrophotometer with an ATR element for multiple internal reflections for measuring the concentration of specific substances in a liquid. However, this infrared spectrophotometer consists of a complex and extensive arrangement, which among others is provided with mirrors in separate housings and with a disk with filters driven by a motor via a transmission. For this reason, such a spectrophotometer cannot easily be placed in an oil circuit of a compressor.

Moreover, tests have shown that the measurement results of such an infrared spectrophotometer during use in the oil circuit of a compressor are greatly disturbed by the uneven heating of the components of the infrared spectrophotometer as a result of the temperature of the oil in the oil circuit and the temperature of the environment whereby both temperatures can vary.

SUMMARY OF THE INVENTION

The present invention is intended to provide a solution to one or more of the aforementioned and/or other disadvantages. To this end the invention concerns an oil sensor that comprises a holder to which an elongated crystal is fastened that is transparent to infrared light and with a refractive index greater than the refractive index of the oil to be examined, whereby a light source is provided in the holder at a first end of the elongated crystal for transmitting light in the infrared spectrum in the elongated crystal, and detection means at a second end of the elongated crystal for measuring the intensity of the light, which during the passage through the elongated crystal undergoes total reflection at a boundary plane at least four times in succession in a contact zone where the elongated crystal comes into contact with the oil to be examined, and whereby the oil sensor is further provided with at least one temperature sensor to determine the temperature of at least one of the components of the oil sensor, and that the part of the light source that can emit light can be heated to a temperature of more than 400° C.

An advantage of an oil sensor according to the present invention is that such an oil sensor enables it to be affixed in an oil circuit of a compressor in order to measure a property of the oil at discrete times or continuously, whereby this property is a measure of the ageing of the oil.

Another advantage of an oil sensor according to the invention is that it enables specific changes in the oil in compressors to be measured over a long usage duration and with great sensitivity. The oil sensor according to the invention can also be used to measure changes in engine oil, in particular when great sensitivity is desired.

The aforementioned elongated crystal is an ATR element for multiple internal reflection at a boundary plane that is brought into contact with the oil to be examined. ATR stands for attenuation of the total reflection. The elongated crystal has a higher refractive index than the oil to be examined. Preferably the elongated crystal has a refractive index greater than 1.6, in particular greater than 1.9 and preferably greater than 2.2.

As light in the ATR element is incident on the boundary plane with the oil at an angle greater than the critical angle, according to Snell's law total internal reflection occurs, whereby the light is reflected at the same angle as the incident angle.

When a part of the light is absorbed by the oil at the boundary plane attenuation occurs. The spectrum of this attenuation, or in other words the change of the attenuation as a function of the wavelength, is representative of the composition of the oil and is determined by vibrations of molecules that are excited by the light.

In an elongated crystal the light is thus reflected a number of times and a part of the light can be absorbed by the oil at the boundary plane each time: thus due to the multiple internal reflections the total attenuation increases, which increases the sensitivity of the oil sensor.

Thus the oil sensor is suitable for measuring small changes as a result of ageing in an oil for compressors over a long usage duration, for example by measuring in wavelength bands in which molecules and/or functional groups of molecules and/or certain bonds of molecules are excited, which increase or decrease as a result of degradation processes so that the measurement is a measure of the ageing of the oil. The molecules and/or functional groups of molecules and/or certain bonds of molecules can occur in the oil itself or in the additives to the oil, or can also occur as a result of a process during use of the oil.

Preferably the elongated crystal is dimensioned such that the diameter of the smallest sphere that the crystal encloses is at least four times greater than the largest sphere that can be inscribed in the elongated crystal.

In a practical embodiment of the elongated crystal at least partially consists of zinc selenide, zinc sulphide, arsenic sulphide, silver halide, gallium arsenide, germanium, silicon, zirconium oxide, KRS-5, KRS-6, sapphire, Gasir® and/or diamond. The elongated crystal can also entirely or partially consist of non-crystalline material.

According to a particular variant embodiment, the elongated crystal can be provided with a coating, at least partially in the zone where the crystal comes into contact with the oil to be examined. Such a coating can for example improve the chemical and/or wear resistance of the elongated crystal for the oil to be examined. The coating can also be used to counteract depositions on the elongated crystal. A DLC coating can be applied as a coating for example, whereby DLC stands for diamond-like carbon.

Preferably a seal is affixed around the elongated crystal at both ends between the holder and the elongated crystal, and the seal is constructed and/or mounted such that it enables an expansion of the elongated crystal on at least one side.

Such a seal can be made of standard sealing materials or otherwise such as: EPDM, NBR, Viton®, Kalrez®, silicone and similar, or any combination of such and/or other materials.

This oil sensor can be placed in the oil circuit of a compressor in a simple way.

Preferably the aforementioned elongated crystal is cylindrical or tubular. Preferably at least one end of this elongated crystal is conically bevelled off.

It has been found that with a cylindrical elongated crystal with a length of at least 10 mm, in particular at least 20 mm, preferably at least 40 mm and a maximum diameter of 7 mm, in particular a maximum of 5 mm, preferably a maximum of 3 mm, good measurements are possible.

It has also been found that with a curved cylindrical elongated crystal with a length of at least 10 mm, in particular at least 20 mm, preferably at least 40 mm and a diameter between 0.3 and 2 mm, good measurements are possible.

With a curved cylindrical elongated crystal "mode mixing" occurs, which increases the measurement sensitivity. Thus with a curved cylindrical elongated crystal, less light is needed for the same measurement sensitivity than for a non-curved cylindrical elongated crystal. For example, with a curved cylindrical elongated crystal a smaller diameter can be used, which is also suitable in practice to be able to give the elongated crystal a curved form.

It has been found that to be able to make the curved cylindrical elongated crystal, and also to obtain a sufficient measurement sensitivity, preferably a part of the axis of the curved cylindrical elongated crystal has a radius of curvature that is greater than five times, preferably 10 times, and less than forty times, preferably twenty times the radius of the largest sphere that can be inscribed in the curved cylindrical elongated crystal.

For a practical compact construction, preferably the length of the axis of the curved cylindrical elongated crystal is greater than three times, preferably five times, the radius of the smallest sphere that the elongated crystal encloses.

In a practical embodiment, the curved cylindrical elongated crystal presents one or more loops. Preferably these loops do not touch one another, so that the oil to be examined can easily flow everywhere along the surface of the curved cylindrical elongated crystal and the measurement of the oil sensor correctly reflects the state of the oil in the oil circuit.

It has also been found that with a tubular crystal with a ratio of the inside diameter to outside diameter of between 0.3 and 0.9, in particular between 0.5 and 0.9, and preferably between 0.7 and 0.9, the number of internal reflections increases strongly, to almost double, with respect to a cylindrical elongated crystal that is just as long, with little or no reduction of the intensity of the light that occurs at the second end of the elongated crystal with respect to the intensity that is transmitted into the elongated crystal at the first end.

A concentric reflector can also be affixed in the tubular elongated crystal and/or the tubular elongated crystal can be filled with air or another gas. The tubular elongated crystal can also be filled with a solid material.

It has been found that with a corrugated construction of the surface of the elongated crystal that can come into contact with the oil to be examined, and by providing this surface with peaks and troughs that are approximately parallel to the longitudinal direction of the elongated crystal, the number of internal reflections increases strongly, to almost double.

The oil sensor according to the present invention is also provided with at least one temperature sensor in order to determine the temperature of at least one of the components of the oil sensor. On the basis of reference measurements at different temperatures of the oil in the oil circuit and different temperatures of the environment, using the temperature measured by one or more of these temperature sensors, the measurement of the oil sensor can be converted to a reference state so that accurately small changes in the oil as a result of ageing over a long usage duration of the oil in the compressor can be measured.

In a practical embodiment of the present invention the aforementioned light source is a thermal emitter, in which a filament or a membrane can be electrically heated to a temperature of more than 400° C., in particular more than 500° C., and preferably more than 600° C. in order to emit light. A possible light source is for example the type MIRL17-900 of Intex. The light source can operate continuously, pulsed, or intermittently.

An oil sensor according to the present invention can further be provided with an input reflector to transmit more light emitted by the light source into the elongated crystal so that it is incident on the boundary plane of the elongated crystal with the oil at an angle greater than the critical angle. With such an input reflector, for the same desired light output, a light source with a lower power can be used that is cheaper and smaller. A compact embodiment can be obtained as the input reflector largely encloses the shortest path between the light source and the first end of the elongated crystal.

An oil sensor according to the present invention can also be provided with an output reflector to transmit more light to the detection means after passing through the elongated crystal. Such an output reflector can increase the sensitivity of the oil sensor for the same detection means. A compact embodiment can be obtained if the output reflector largely encloses the shortest path between the detection means and the second end of the elongated crystal.

In a practical embodiment of the present invention the detection means in the oil sensor can measure the intensity of light with a wavelength between 2,000 and 20,000 nanometres for example.

Preferably the detection means in the oil sensor can measure the intensity of light with a wavelength between 2,000 and 11,000 nanometres, and in particular between 5,000 and 8,000 nanometres. It has been found that the ageing of the oil in a compressor can be well observed in this wavelength range in particular.

In a practical embodiment of the present invention, the detection means comprise a pyroelectric or ferroelectric detector, a thermopile detector, a resistive or diode microbolometer, a photoconductive or photovoltaic detector. The detection means can be provided with a window that only allows through a part of the spectrum of the infrared light to the detection means. By making a suitable choice of the material that the window consists of, the light in a specific wavelength band can be measured with the detection means. The window can also be applied as a coating on the detection means.

Alternatively the window can also be constructed as a Fabry-Perot filter whereby the part of the infrared light allowed through to the detection means can be controlled. For example with successive different settings of the Fabry-Perot filter, the light in the corresponding different wavelength bands can be measured.

In a practical embodiment, a grating is placed in the optical path between the second end of the elongated crystal and the detection means, such that at least part of the light undergoes diffraction before it is incident on the detection means. Alternatively, a prism is placed in the optical path between the second end of the elongated crystal and the detection means, such that at least a part of the light undergoes refraction before it is incident on the detection means.

In a practical embodiment, a bandpass filter is provided in the optical path between the second end of the elongated crystal and the detection means, such that at least a part of the light is filtered to a greater or lesser extent according to the wavelength before it is incident on the detection means.

By selecting the light that is incident on the detection means in this way, the measurement sensitivity and/or selectivity of the oil sensor can be increased, in particular for measuring the ageing of compressor oil, and/or cheaper detection means can be used.

The present invention also concerns an oil sensor whereby the detection means comprise a number of detectors, each possibly provided with a certain window so that the light can be measured in a number of wavelength bands. An example of such a detector is the LIM-011 of Infratec.

The detection means can also consist of a matrix of pixels like an image sensor, with zones for which a certain window is affixed, possibly also as a coating, so that by selecting certain zones of pixels a certain wavelength band can be measured.

According to the invention the detection means can comprise a number of detectors, whereby a central detector can measure the intensity of a part of the light that is emitted by the light source and is directly incident on the detection means, thus according to an approximately straight line from the light source to this central detector. The temperature of the light source can also be determined with this central detector.

In a practical embodiment, the conical bevelled ends of the cylindrical elongated crystal can be truncated, so that a part of the light emitted by the light source goes through the cylindrical elongated crystal approximately along the axis and is directly incident on the central detector. Preferably a screen is affixed around the central detector to prevent light that does not come directly from the light source getting to the central detector.

The present invention also concerns an oil sensor whereby the elongated crystal is detachable. In this way the elongated crystal can be cleaned, for example by rinsing or immersion in a suitable liquid such as a solvent. In this way the elongated crystal can also be replaced, for example in the event of damage or incorrect operation.

The present invention also concerns an oil sensor whereby more than one elongated crystal is fastened to the holder.

The present invention also concerns a compressor whose oil circuit is provided with such an oil sensor. Preferably the oil sensor in the oil circuit of a compressor is provided downstream from a cooler and upstream from an oil injection in the compression space of a compressor element or in the bearings or between gearwheels, by which the compressor element is driven and/or the rotors are synchronised.

The present invention also concerns a method for determining the extent of ageing of oil that circulates in a compressor, vacuum pump or expander during a certain time interval, whereby this method comprises the following steps:
  bringing an oil sensor according to the invention into contact with a part of the oil that circulates;
  measuring the intensity of the light in a certain wavelength band after passing through the elongated crystal a first time at the start of the aforementioned time interval, and a second time at the end of the aforementioned time interval; and
  determining the extent of ageing of the oil during that time interval as the change of the measured intensity of the light in this wavelength band between the two measurements.

Preferably the wavelength band is chosen such that after ageing the oil to be examined presents a different infrared absorption in this wavelength band.

The present invention also concerns the following method. First an oil sensor according to the invention is brought into contact with a part of the oil that circulates. With the oil sensor according to the invention the intensity of the light after passing through the elongated crystal is measured in a certain wavelength band and in a reference wavelength band at a first point in time at the start of a time interval and a first ratio between the two is determined. At a second point in time at the end of the time interval, after passing through the elongated crystal the light in the specific wavelength band and in the reference wavelength band is measured a second time and a second ratio between the two is determined. The extent of ageing during the elapsed time interval can then be determined as the change of the second ratio with respect to the first ratio. Preferably, the reference wavelength band is chosen such that the oil sensor measures little or no difference between unused oil and oil at the end of the specified usage duration of the oil.

An advantage of this method is that the extent of ageing thus determined is not affected by the possible change of the light source and/or the detection means over time, for example the lower emission of light by the light source and/or the measurement of a smaller value by the detection means for the same light intensity.

The present invention also concerns the following method. The temperature of at least one of the components of the oil sensor is measured and the measurement of the oil sensor is corrected for this measured temperature. In this way, for example, reference measurements can be made on an oil that has not aged at different temperatures of a component of the oil sensor, for example as a result of different oil temperatures and/or environmental temperatures. Using well known interpolation techniques the measurement of the oil sensor can then be corrected on the basis of the measured temperature of that component.

An advantage of this method is that the thus corrected measurement of the oil sensor is not influenced, or less so, by varying temperatures of the components of the oil sensor.

A method according to the present invention can also comprise a step whereby the power of the light source is controlled such that in a certain wavelength band the oil sensor measures a certain value. In this way the extent of ageing of the oil measured by the oil sensor is not influenced, or less so, by the possible change of the light source and/or the detection means and/or other components of the oil sensor under the influence of temperature and/or time for example.

According to the invention the measurements of the oil sensor can also be presented on a display of the compressor. In this way the user and/or maintenance technician can check the ageing of the oil. It is also possible that the measurements of the oil sensor are passed on via a network to be able to check the ageing of the oil of this compressor remotely.

According to the invention the measurements of the oil sensor can also be passed on to the controller of the compressor, for example when predetermined limits are exceeded for the ageing of the oil to activate an audio and/or visual alarm, and/or to limit the operation of the compressor to certain limits in order to prevent wear and/or damage to the compressor due to the less effective cooling and/or lubrication of the aged oil.

BRIEF DESCRIPTION OF THE DRAWINGS

With the intention of better showing the characteristics of the invention, a few preferred embodiments of an oil sensor according to the invention are described hereinafter by way of an example, without any limiting nature, with reference to the accompanying drawings, wherein.

DETAILED DESCRIPTION OF THE INVENTION

Figure 1:
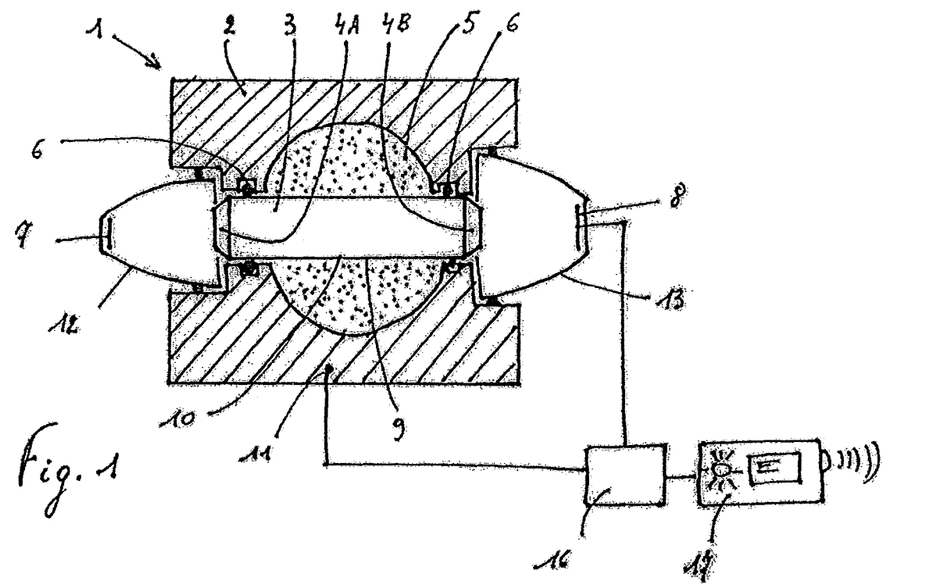
FIG. 1 schematically shows an oil sensor according to the invention.

FIG. 1 shows an oil sensor 1 according to the invention that is provided with a holder 2. In this case a first pipe, not shown in the drawing, is coupled to the holder 2 on the one side transversely with respect to the oil sensor 1, in order to carry the oil 5 to be examined to the oil sensor, and on the other side a second pipe, not shown, to carry the oil 5 to be examined away from the oil sensor 1.

An ATR element is provided in the aforementioned holder 2 for multiple internal reflections at a boundary plane 9 that can be brought into contact with the oil 5 to be examined, whereby this ATR element according to the invention is constructed in the form of a cylindrical elongated crystal 3. The elongated crystal 3 concerned is, in this case but not necessarily, conically bevelled off at the first end 4A and at the second end 4B.

Preferably but not necessarily, a seal 6 is provided at both ends 4A and 4B between the holder 2 and the cylindrical elongated crystal 3, all such that the cylindrical elongated crystal 3 can expand and contract with respect to the holder 2. However, the invention is not limited as such, as such a seal can also be provided at only one end 4A or 4B for example.

The cylindrical elongated crystal 3 is transparent to infrared light and has a refractive index that is greater than the refractive index of the oil 5 to be examined.

In a contact zone 10 that extends to the outside of the elongated crystal 3 between the seals 6 at both ends 4A and 4B, the elongated crystal 3 can be brought into contact with the oil 5 to be examined.

At the aforementioned first end 4A of the cylindrical elongated crystal 3, the holder 2 is provided with a light source 7, in this case a thermal emitter.

Furthermore, preferably an input reflector 12 is provided on the holder 2, whereby this input reflector 12 almost completely encloses the shortest path between the light source 7 and the first end 4A of the cylindrical elongated crystal 3.

At the aforementioned second end 4B of the cylindrical elongated crystal 3, the holder 2 is provided with detection means 8.

Furthermore, the oil sensor 1 comprises an output reflector that can be fastened to the holder 2 and which almost completely encloses the shortest path between the detection means 8 and the nearby second end 4B of the cylindrical elongated crystal 3.

According to the invention, the oil sensor 1 is further provided with a temperature sensor 11 that is configured such that it can determine the temperature of at least one of the components of the oil sensor 1, in this case of the holder 2, by the temperature sensor 11 being mounted in or on this holder 2.

The detection means 8 and the temperature sensor 11 are connected to a processing unit 16, for example in the form of a computer, which is able to interpret and/or process the signals generated by the detection means 8 concerned and the temperature sensor 11, and on the basis of this directly or indirectly control signalling means 17. These signalling means 17 can be visual, for example a lamp or display screen, or audio, for example a buzzer.

The processing unit 16 can also receive and use signals generated by the light source 7 according to a connection, not shown in the drawing, for example a temperature measurement in order to interpret and/or process the signals generated by the detection means 8.

The oil sensor 1 according to FIG. 1 is compact and can easily be placed in the oil circuit of a compressor. The determination of the ageing of the oil by this oil sensor 1 is simple and can be done as follows.

Figure 2:
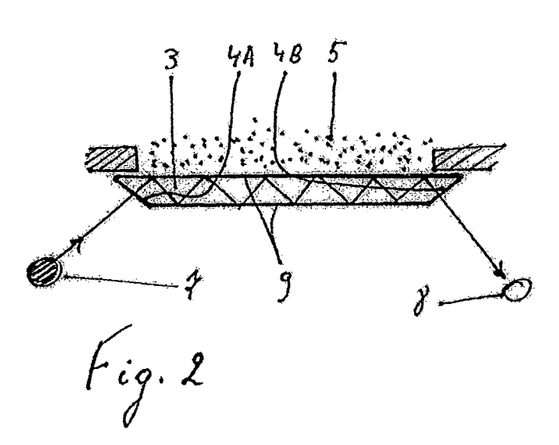
FIG. 2 schematically shows the operation of the oil sensor according to FIG. 1.

The operation of the oil sensor according to the invention is discussed on the basis of FIG. 2, which shows that the light source 7 at the first end 4A transmits light into the elongated crystal, such that this light is incident at an angle greater than the critical angle on a boundary plane 9 between the elongated crystal 3 and the oil 5 to be examined that is guided along the crystal 3.

At the boundary plane 9 the light is repeatedly reflected internally in the elongated crystal 3. Whenever the light is incident on the boundary plane 9 a part of this light can be absorbed. A part of the light exits the crystal 3 as an evanescent wave and is absorbed in the oil 5 to be examined. The absorption in the oil 5 to be examined can be done by excitation by the light of molecules and/or functional groups of molecules and/or certain bonds of molecules that are present in the oil 5 to be examined or in the additives of the oil 5 to be examined, or which occur as a result of a process during use of the oil 5 to be examined.

At the second end 4B the detection means 8 measure the intensity of the light after passing through the elongated crystal 3.

Figure 3:
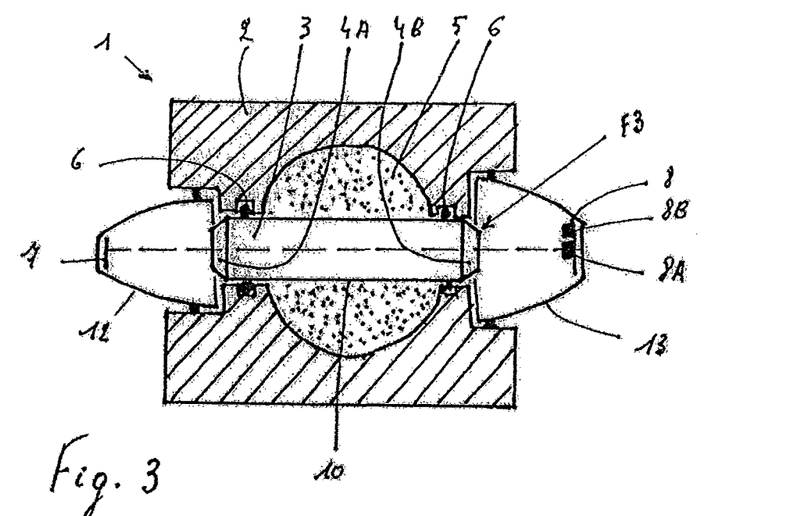
FIG. 3 shows a variant of an oil sensor according to FIG. 1.

FIG. 3 shows a variant of the oil sensor according to the invention. The detection means 8 comprise two detectors, i.e. a central detector 8A and a second detector 8B.

The intensity of the light is measured by the second detector 8B in a wavelength band in which the oil 5 to be examined exhibits absorption upon ageing.

The central detector 8A measures the intensity of a part of the light that is transmitted by the light source 7 and is incident on the central detector 8A according to an approximately straight line. The central detector 8A hereby acts as a temperature sensor by measuring the intensity of the light source 7 that is a measure of the temperature of the light source 7.

Then at a first point in time, a first ratio is determined between the intensity measured by the second detector 8B and the central detector 8A.

Then at a second point in time, a second ratio is determined between the intensity measured by the second detector 8B and the central detector 8A.

The extent of ageing during the time interval between the first and second point in time is then determined as the change of the second ratio at the second point in time with respect to the first ratio at the first point in time.

Figure 4:
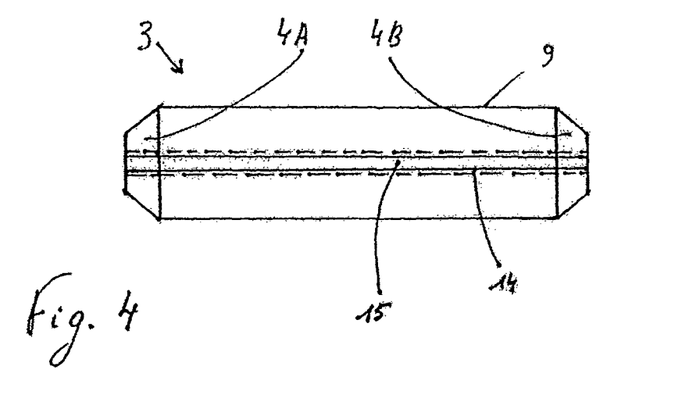
FIG. 4 shows another embodiment of the section that is indicated in FIG. 3 by arrow F3.

FIG. 4 shows a tubular elongated crystal 3 that is bevelled at both ends 4A and 4B. In the cavity 15 there is a concentric reflector 14. At the first end 4A light is sent into the tubular elongated crystal 3, such that this light is incident on the boundary plane 9 at an angle greater than the critical angle. The light is reflected at the boundary plane 9 and is then incident on the concentric reflector 14. There the light is reflected after which it is incident again on the boundary plane 9. Thus the light is repeatedly reflected internally in the tubular elongated crystal 3 and whenever the light is incident on the boundary plane 9 a part of the light can be absorbed.

According to the invention the elongated crystal 3 can also be somewhat bent or even have a fully curved form.

The holder 2 can also be constructed such that the oil sensor can be affixed as a probe in an opening in a pipe.

The input reflector 12 and/or output reflector 13 can also have another form and entirely or partially form part of the holder 2. The input reflector 12 and/or output reflector can also consist of a number of reflectors, that can be curved both concave and convex. The input reflector 12 and/or output reflector can also be provided with lenses to converge or diverge a part of the light.

The central detector 8A can also be at a distance from the other detection means 8. In addition to a first detector 8B, the detection means 8 can also comprise more detectors.

The materials of the components of the oil sensor 1 can be chosen such that they experience little influence from thermal expansion.

The components of the oil sensor can be fastened to the holder by screws, adhesive, a snap-in system or another fastening means.

The present invention is by no means limited to the embodiments described as an example and shown in the drawings, but an oil sensor according to the invention can be realised according to different variants without departing from the scope of the invention.

Figure 5:
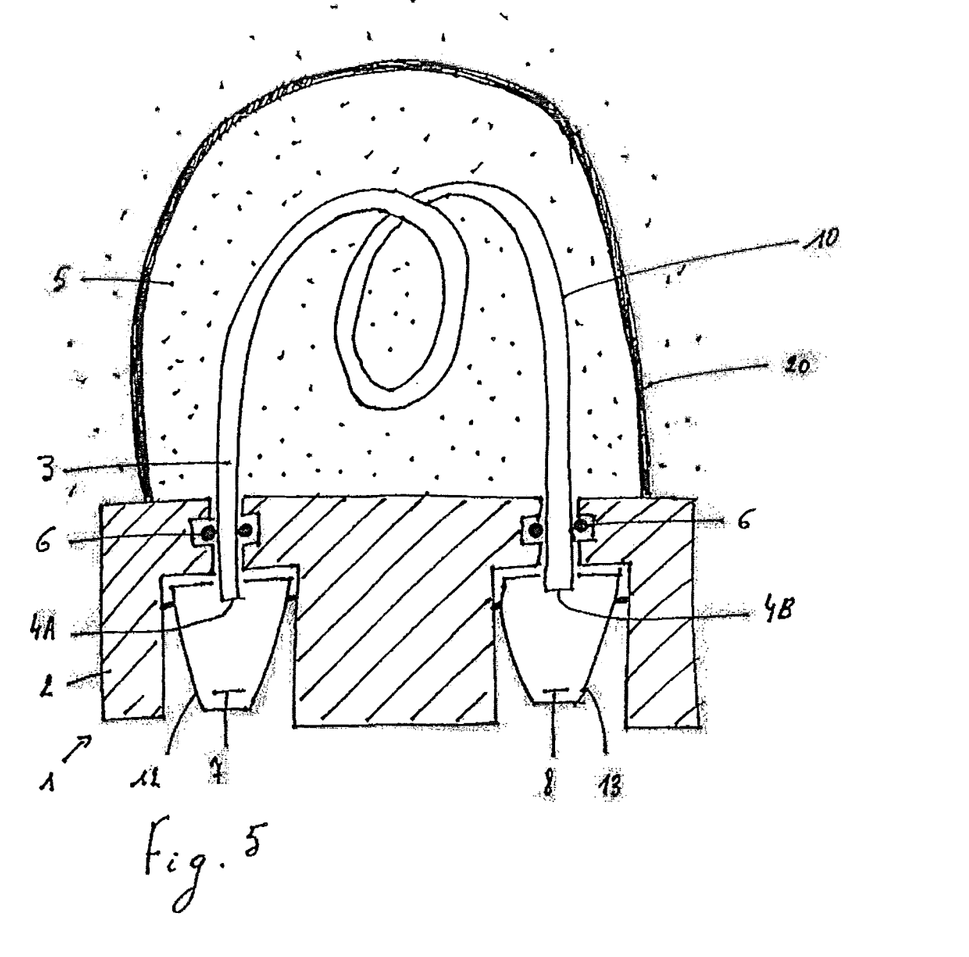
FIG. 5 shows a variant of an oil sensor according to FIG. 1 with a curved cylindrical elongated crystal.

FIG. 5 shows a variant of the oil sensor 1 with a curved cylindrical elongated crystal 3. In this case the curved cylindrical elongated crystal 3 presents one loop.

Furthermore, a clasp 20 is fastened to the holder 2 to protect the curved cylindrical elongated crystal 3, for example against jolts when mounting the oil sensor 1. Instead of a clasp 20 another type of screen can be used, for example a cage.

Figure 6:
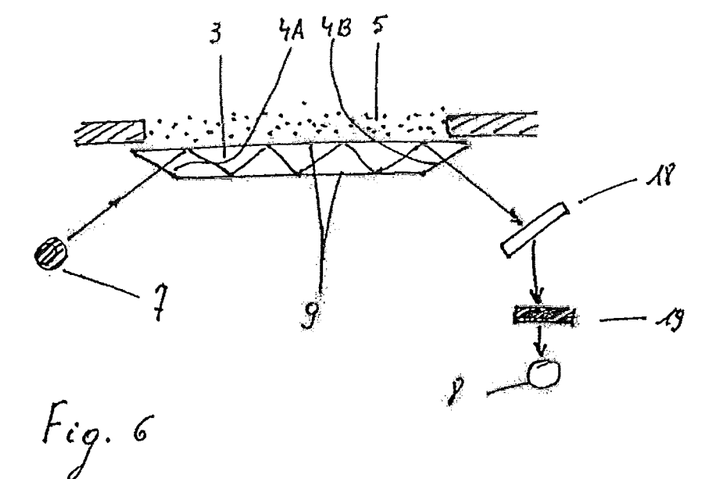
FIG. 6 schematically shows the operation of a variant of the oil sensor of FIG. 2.

FIG. 6 schematically shows the operation of a variant of the oil sensor 1 of FIG. 2.

An optical element 18 is placed between the second end 4B and the detection means 8. This optical element 18 enables a part of the incident light to exit at a different angle according to the wavelength, for example by means of diffraction or refraction. For diffraction a grating can be used as an optical element 18, either in transmission or in reflection, or a prism for refraction.

Between the optical element 18 and the detection means 8 a bandpass filter 19 is deployed that filters a part of the light to a greater or lesser extent according to the wavelength.

Thus the detection means 8 can selectively measure the light in certain wavelength bands after passing through the elongated crystal 3.

The invention claimed is:

1. An oil sensor comprising:
    a holder to which an elongated crystal is fastened that is transparent to infrared light and with a refractive index greater than a refractive index of oil to be examined,
    wherein a light source is provided in the holder at a first end of the elongated crystal for transmitting light in the infrared spectrum along an axial length of the elongated crystal, and a detector at a second opposite end of the elongated crystal for measuring an intensity of the light, which during passage through the axial length of the elongated crystal undergoes total reflection at a boundary plane at least four times in succession in a contact zone where the elongated crystal comes into contact with the oil to be examined,
    wherein the oil sensor is further provided with at least one temperature sensor to determine the temperature of at least one of the components of the oil sensor, and that the part of the light source that is provided in the holder that emits light is configured to be heated to a temperature of more than 400° C., and
    wherein the elongated crystal is tubular and has a ratio of an inside diameter to an outside diameter between 0.3 and 0.9.

2. The oil sensor according to claim 1, wherein the part of the light source that can emit light can be heated to a temperature of more than 500° C. and preferably more than 600° C.

3. The oil sensor according to claim 2, wherein the part of the light source that can emit light is a membrane that can be heated as an electrical resistor.

4. The oil sensor according to claim 1, wherein the light source is constructed in the form of an intermittent and/or pulsing light source.

5. The oil sensor according to claim 1, wherein an input reflector that is fastened to the holder is configured such that this input reflector can receive a part of the light originating from the light source and send it into the elongated crystal.

6. The oil sensor according to claim 5, wherein at least 50%, preferably at least 75% of the shortest path between the light source and the first end of the elongated crystal is in the volume enclosed by the input reflector.

7. The oil sensor according to claim 1, wherein an output reflector that is fastened to the holder is configured such that this output reflector can receive a part of the light, after passing through the elongated crystal, and transmit it to the detector.

8. The oil sensor according to claim 7, wherein at least 50%, preferably at least 75% of the shortest path between the detector and the nearby second end of the elongated crystal is in the volume enclosed by the output reflector.

9. The oil sensor according to claim 1, wherein the elongated crystal is configured such that light emitted by the light source, when passing through the elongated crystal, undergoes total reflection at least eight times at the boundary plane in the contact zone where the elongated crystal comes into contact with the oil to be examined, in particular at least twelve times, preferably at least twenty times before reaching the detector.

10. The oil sensor according to claim 1, wherein the detector is constructed to measure the intensity in two or more wavelength bands.

11. The oil sensor according to claim 10, wherein the detector is constructed to measure the intensity in three or more wavelength bands, preferably in four wavelength bands.

12. The oil sensor according to claim 1, wherein the detector also comprises a central detector that can measure the intensity of a part of the light that is emitted by the light source and is incident on the central detector along an approximately straight line.

13. The oil sensor according to claim 1, wherein a seal is affixed between the holder and the elongated crystal around the elongated crystal at the first end or the second end, that enables expansion of the elongated crystal on at least one end.

14. The oil sensor according to claim 1, wherein the elongated crystal is cylindrical.

15. The oil sensor according to claim 1, wherein the detector comprises a pyroelectric or ferroelectric detector.

16. The oil sensor according to claim 1, wherein the detector comprises a thermopile detector.

17. The oil sensor according to claim 1, wherein the detector comprises a resistive or diode microbolometer, photoconductive or photovoltaic detector.

18. A compressor, expander or vacuum pump, comprising an oil sensor according to claim 1.

19. A method for determining the extent of ageing of oil that circulates in a compressor, vacuum pump or expander during a certain time interval, comprising the following steps:
    bringing an elongated crystal of an oil sensor into contact with a part of oil that circulates in the compressor, vacuum pump or expander, wherein the oil sensor comprises a holder to which the elongated crystal is fastened that is transparent to infrared light and with a refractive index greater than a refractive index of the oil to be examined, said elongated crystal being tubular and having a ratio of an inside diameter to an outside diameter between 0.3 and 0.9;

transmitting light from the infrared spectrum along an axial length of the elongated crystal from a light source provided in the holder at a first end of the elongated crystal;

measuring the intensity of the light with a detector at a second opposite end of the elongated crystal in a certain wavelength band after passing through the elongated crystal a first time at the start of the aforementioned time interval, and a second time at the end of the aforementioned time interval, wherein the transmitted light that passes through the axial length of the elongated crystal undergoes total reflection at a boundary plane at least four times in succession in a contact zone where the elongated crystal comes into contact with the oil to be examined; and determining the extent of ageing of the oil during that time interval as a change of the measured intensity of the light in this wavelength band between the two measurements.

20. A method for determining the extent of ageing of oil over a certain time interval that circulates in a compressor, expander or vacuum pump, comprising the following steps:

bringing an elongated crystal of an oil sensor according into contact with a part of oil that circulates in the compressor, vacuum pump or expander, wherein the oil sensor comprises a holder to which the elongated crystal is fastened that is transparent to infrared light and with a refractive index greater than a refractive index of the oil to be examined, said elongated crystal being tubular and having a ratio of an inside diameter to an outside diameter between 0.3 and 0.9;

transmitting light from the infrared spectrum along an axial length of the elongated crystal from a light source provided in the holder at a first end of the elongated crystal;

at a first point in time, measuring the intensity of the light at a second opposite end of the elongated crystal in a certain wavelength band and in a reference wavelength band after passing through the axial length of the elongated crystal at the start of the aforementioned time interval, and a determination of a first ratio between the two;

at a second point in time, the intensity of the light is measured in the certain wavelength band and in the reference wavelength band after passing through the axial length of the elongated crystal at the end of the aforementioned time interval, and a determination of a second ratio between the two, wherein the transmitted light that passes through the axial length of the elongated crystal undergoes total reflection at a boundary plane at least four times in succession in a contact zone where the elongated crystal comes into contact with the oil to be examined; and determining the extent of ageing of the oil during the elapsed time interval on the basis of a change of the second ratio with respect to the first ratio.

* * * * *